(12) United States Patent
Kim et al.

(10) Patent No.: US 6,720,434 B2
(45) Date of Patent: Apr. 13, 2004

(54) PROCESS FOR PREPARING CHIRAL COMPOUNDS FROM RECEMIC EPOXIDES BY USING CHIRAL SALEN CATALYSTS

(75) Inventors: Geon-Joong Kim, Seoul (KR); Dae-Woon Park, Seoul (KR); Ho Seong Lee, Daejeon (KR); Jin Won Yun, Choongcheong-bookdo (KR); Seong Jin Kim, Daejeon (KR)

(73) Assignee: RSTECH Co., Ltd., Daejeon (KR)

( * ) Notice: Subject to any disclaimer, the term of this patent is extended or adjusted under 35 U.S.C. 154(b) by 0 days.

(21) Appl. No.: 10/181,193

(22) PCT Filed: May 23, 2001

(86) PCT No.: PCT/KR01/00854

§ 371 (c)(1),
(2), (4) Date: Jul. 11, 2002

(87) PCT Pub. No.: WO01/89690

PCT Pub. Date: Nov. 29, 2001

(65) Prior Publication Data

US 2003/0032821 A1 Feb. 13, 2003

(30) Foreign Application Priority Data

May 24, 2000 (KR) ........................................ 2000-28099

(51) Int. Cl.$^7$ ........................ C07D 301/04; C07C 31/20
(52) U.S. Cl. ...................................... 549/523; 568/859
(58) Field of Search ................................ 502/152, 167; 549/523; 568/859

(56) References Cited

U.S. PATENT DOCUMENTS 5,665,890 A * 9/1997 Jacobsen et al. ............ 549/230
5,929,232 A * 7/1999 Jacobsen et al. ............ 540/145

FOREIGN PATENT DOCUMENTS

WO          91/14694      * 10/1991

OTHER PUBLICATIONS

Annis et al., *Polymer–Supported Chiral Co(Salen) Complexes: Synthetic Applications and Mechanistic Investigations in the Hydrolytic Kinetic Resolution of Terminal Epoxides*, J. Am. Chem. Soc., 1999, vol. 121, pp. 4147–54.
Baldwin et al., *Synthesis of (R)– and (S)–Epichlorohydrin*, J. Org. Chem., 1978, vol. 43, No. 25, pp. 4876–78.
Coffee et al., *Preparation of (βS)–N,N–1, 7–Bix–tert–butoxycarbonyl–3–hydroxyspermidine in High Enantiomeric Purity*, J. Org. Chem., 1999, vol. 64, pp. 8741–42.

Irie et al., *Catalytic Asymmetric Epoxidation of Unfunctionalized Olefins Using Chiral (Salen)manganese(III) Complexes*, Tetrahedron: Asymmetry vol. 2, No. 7, pp. 481–494, 1991.

Irie et al., *Enantioselective Epoxidation of Unfunctionlized Olefins Using Chiral (Salen)Manganese(III) Complexes*, Tetrahedron Letters, 1991, vol. 32, pp. 1055–58.

Jacobsen et al., *Enantioselective Catalytic Ring Opening of Epoxides with Carboxylic Acids*, Tetrahedron Letters, 1997, vol. 38, No. 5, pp. 773–76.

Larrow et al., *A Practical Method for the Large–Scale Preparation of [N,N$^1$–Bis(3,5–di–tert–butylsalicylidene)–1, 2–cyclohexanediaminato(2–)]manganese(III) Chloride, a Highly Enantioselective Epoxidation Catalyst*, J. Org. Chem., 1994, pp. 1939–42.

Orita et al., *Distannoxane–Catalyzed Selective Acetylation of 3–Chloropropane–1,2–diol: A Convenient Synthesis of Enantiopure Epichlorohydrin*, Synlett, 1999, No. 12, pp. 1927–29.

Takano et al., *Practical Synthesis of (R)–γ–Amino–β–Hydroxybutanoic Acid (Gabor) from (R)–Epichlorohydrin*, Tetraheydron Letters, 1987, vol. 28, No. 16, pp. 1783–84.

Tokunaga et al., *Asymmetric Catalysis with Water: Efficient Kinetic Resolution of Terminal Epoxides by Means of Catalytic Hydrolysis*, Science, 1977, vol. 277, Aug. 15, pp. 936–38.

Zhang et al., *Enantioselective Epoxidation of Unfunctionalized Olefins Catalyzed by (Salen)manganese Complexes*, J. Am. Chem. Soc., 1990, pp. 2801–03.

* cited by examiner

*Primary Examiner*—Taofiq Solola
(74) *Attorney, Agent, or Firm*—Jones Day

(57) ABSTRACT

The present invention relates to chiral salen catalysts and a process for preparing chiral compounds from racemic epoxides by using them. More particularly, the present invention is to provide chiral salen catalysts and its use for producing chiral compounds such as chiral epoxides and chiral 1,2-diols economically in high yield and high optical purity by performing stereoselective hydrolysis of racemic epoxides, wherein the chiral salen catalyst comprises a cationic cobalt as a center metal of chiral salen ligand and counterions having weak nucleophilic property to resolve disadvantages associated with conventional chiral salen catalysts, and can be used continuously without any activating process of used catalysts because it does not loose a catalytic activity during the reaction process.

2 Claims, 3 Drawing Sheets

PROCESS FOR PREPARING CHIRAL COMPOUNDS FROM RECEMIC EPOXIDES BY USING CHIRAL SALEN CATALYSTS

BACKGROUND OF THE INVENTION

Field of the Invention

The present invention relates to chiral salen catalysts and a process for preparing chiral compounds from racemic epoxides by using them. More particularly, the present invention is to provide chiral salen catalysts and its use for producing chiral compounds such as chiral epoxides and chiral 1,2-diols economically in high yield and high optical purity by performing stereoselective hydrolysis of racemic epoxides, wherein the chiral salen catalyst comprises a cationic cobalt as a center metal of chiral salen ligand and counterions having weak nucleophilic property to resolve disadvantages associated with conventional chiral salen catalysts, and can be used continuously without any activating process of used catalysts because it does not loose a catalytic activity during the reaction process.

Chiral epoxides or chiral 1,2-diols have been widely used to prepare pharmaceuticals and agriculture products having optical properties (U.S. Pat. No. 5,071,868; *Tetrahedron Lett.*, Vol. 28, No. 16, 1783, 1987; *J. Org. Chem.*, Vol. 64, 8741, 1999). Even if these chiral epoxides or chiral 1,2-diols having high optical purity are very useful industrially, use of these compounds has been restricted because the preparation of such compounds is too difficult to produce in a large scale with low manufacturing price.

A preparation method of chiral epichlohydrins as one of chiral expoxides is disclosed using microorganism in EP 431,970 and JP 90-257895 and 94-211822. However, it is not recommended because the productivity is low and it requires two-step process. Another preparation method of chiral epichlohydrins from chiral sulfonyloxyhaloalcohol derivatives obtained from mannitol derivatives is disclosed in U.S. Pat. No. 4,408,063; and *J. Org. chem.*, Vol 43, 4876, 1978. Another preparation method of chiral epichlohydrins from 3-chloro-1,2-propanediol is also disclosed in *Syn. Lett* No. 12, 1927, 1999. However, these processes are required multi-step syntheses, so that they are also deficient to use for the industrial purpose.

Methods for preparing chiral expoxides generally use a chiral catalyst having stereoselectivity which hydrolyzes stereoselectively only one isomer from racemic epoxides mixed 50 and 50 of each isomer and leaves the un-hydrolyzed isomer in the reaction medium. However, the chiral catalyst used for said stereoselective hydrolysis is usually expensive. Therefore, if it cannot be re-used, it becomes difficult to use for the industrial purpose.

Stereoselective hydrolyses of chiral epoxides using chiral salen catalyst as a chiral catalyst are recently disclosed in *Science*, Vol. 277, 936, 1997; U.S. Pat. Nos. 5,665,890 and 5,929,232; and WO00/09463 and WO91/14694. It has been reported that the use of chiral salen catalyst provides higher yield with higher optical purity compared to uses of other chiral catalysts. However, it is reported that after hydrolysis of a racemic epoxide using conventional chiral salen catalyst, the product chiral epoxide is racemized as time goes in pages 86–87 of WO00/09463. When this hydrolysis is performed for mass production, the racemization of the product becomes deepened since it takes longer to perform the distillation to obtain the desired product, thus resulting in decrease of optical purity of the chiral epoxide. Therefore, the use of chiral salen catalyst in the production of chiral epoxides is limited for the above-mentioned reasons.

Further, when conventional chiral salen catalysts are reused, it requires an activation process after each use because activities thereof are rapidly decreased. Even if the catalyst is activated after used, the optical activity of the product prepared by using reused catalyst is remarkably lower than that of the product prepared by using fresh catalyst. Thus, there is limited to reuse. Such problems increase the manufacturing price of producing chiral epoxides.

Consequently, demand to produce chiral compounds such as chiral epoxides or chiral 1,2-diols efficiently and economically has been highly increased with the importance of such compounds to prepare pharmaceuticals and agriculture products.

SUMMARY OF THE INVENTION

The present invention has been completed by developing novel chiral salen catalyst comprising a cobalt as a center metal and its counterions of $PF_6$- or $BF_4$- to prevent from loosing activities of chiral catalysts and racemization of chiral products because conventional chiral salen catalysts having acetate groups loose their activities or functional groups such as acetate groups thereof.

In other words, it is important to select appropriate counterions bonded to the center metal in chiral salen catalysts used in stereoselective hydrolyses of racemic epoxides. For example, chiral catalysts having nucleophilic groups such as acetate and halogen group as counterions deteriorate optical purity of products and counterions bonded weakly to the center metal in chiral catalysts can be dissociated during the reaction process, resulting in diminished catalytic activity.

The chiral salen catalyst of the present invention not only keeps its activity but also provides excellent production of chiral epoxides without racemization by comprising a cobalt center metal and counterions of $PF_6$- or $BF_4$-. Therefore, an object of the present invention is to provide chiral salen catalysts which keep excellent catalytic activity after used, thus simplifing the manufacturing process since it does not require activation process of the used catalyst and do not contribute for racemization of produced products.

Another object of the present invention is to provide an economical process for preparing chiral epoxides and chiral 1,2-diols from racemic epoxides by using said chiral salen catalyst in high yield and high optical purity.

BRIEF DESCRIPTION OF THE PRESENT INVENTION

DETAILED DESCRIPTION OF THE INVENTION

Figure 1:
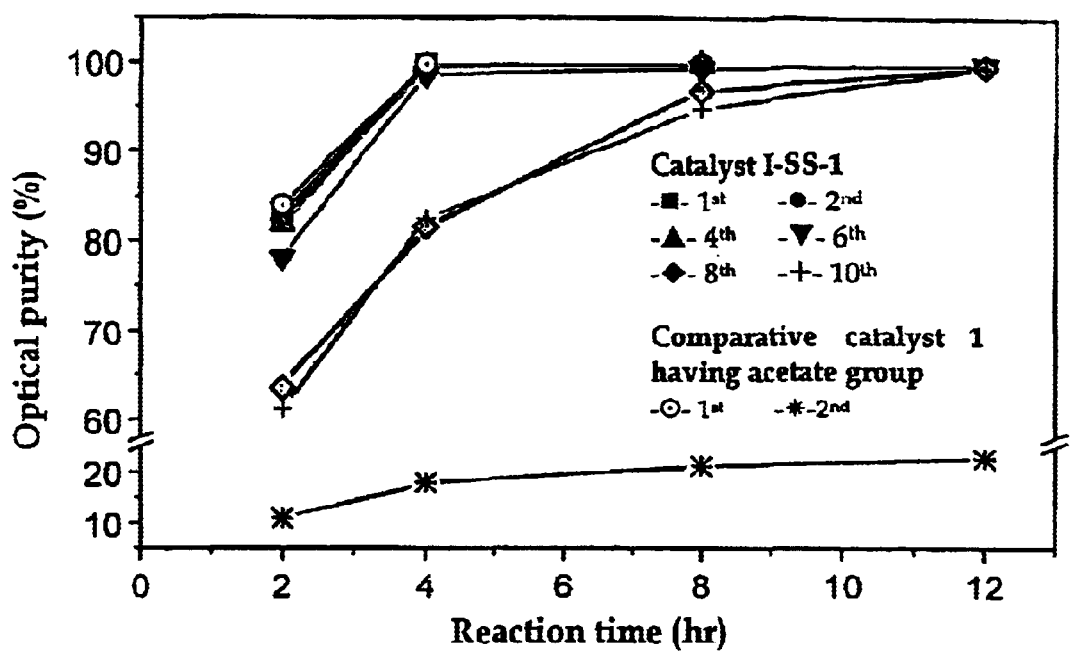
FIG. 1 represents a graph comparing an optical purity of products produced by using conventional chiral salen catalyst having acetate group with that using the chiral salen catalyst of the present invention over reaction time.

The present invention is characterized by using chiral salen catalysts expressed by the following formula (1) in preparation of chiral epoxides or chiral 1,2-diols from racemic epoxides,

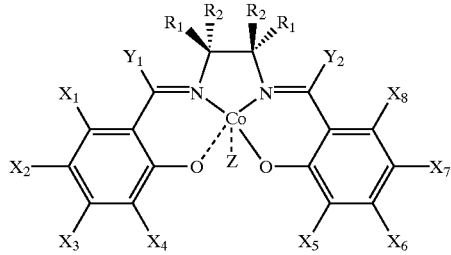

(1)

wherein $X_1$, $X_2$, $X_3$, $X_4$, $X_5$, $X_6$, $X_7$, and $X_8$ represent individually a hydrogen atom or $C_4$–$C_{10}$ alkyl; $Y_1$ and $Y_2$ represent individually a hydrogen atom or $C_1$–$C_5$ alkyl; Z represents $PF_6$, or $BF_4$; $R_1$ and $R_2$ represent individually a hydrogen atom, $C_4$–$C_{10}$ alkyl, or unsubstituted or $C_1$–$C_4$ alkyl substituted phenyl, wherein one of $R_1$ and $R_2$ should be a hydrogen atom, or $R_1$ and $R_2$ are bonded each other to be —$(CH_2)_n$— (where, n is an integer of 3 to 6) or —$(CH_2)_m$—Q—$(CH_2)_m$— (where, m is an integer of 1 to 2, an oxygen atom or NH).

In the stereoselective hydrolysis of racemic epoxides to chiral epoxides or chiral 1,2-diols, the present invention performs in the presence of said chiral salen catalyst of formula (1).

The present invention is described in detail as set forth hereunder.

The present invention relates to the process for preparing optically pure epoxides or 1,2-diols from racemic epoxides by stereoselective hydrolysis in the presence of the chiral salen catalyst which can be reused continuously without an activation process after used and does not affect racemization of the produced products.

The chiral salen catalyst of formula (1) can be easily prepared by a known method disclosed in *Tetrahedron Asymmetry*, Vol. 2, No. 7, 481, 1991; and *J. Org. Chem.*, Vol. 59, 1939, 1994. As shown in Scheme 1, it is prepared by treatment of the salen compound of formula (2) with cobalt (II) acetate and ferrocenium derivative in an organic solvent,

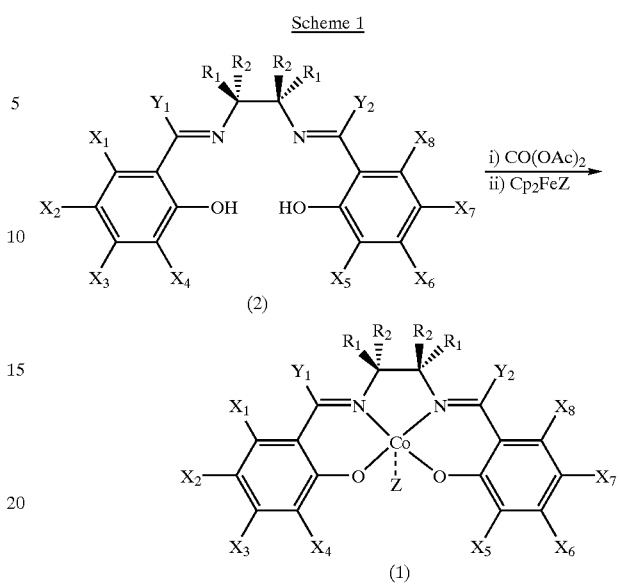

wherein $X_1$, $X_2$, $X_3$, $X_4$, $X_5$, $X_6$, $X_7$, $X_8$, $Y_1$, $Y_2$, Z, $R_1$, and $R_2$ are same as previously defined.

The chiral salen catalyst of formula (1) can be used by immobilizing on the stationary phase such as zeolite.

The mechanism of preparing chiral epoxides or chiral 1,2-diols from racemic epoxides in the presence of the chiral salen catalyst of formula (1) by stereoselective hydrolysis is shown in Scheme 2,

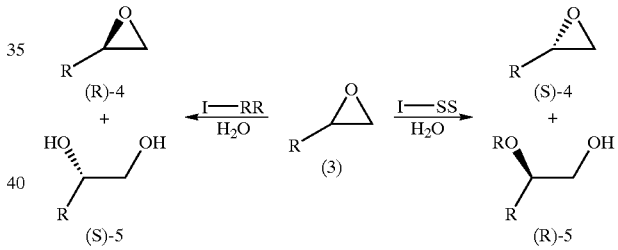

wherein R represents unsubstituted or halogen-substituted $C_1$–$C_{10}$ alkyl, unsubstituted or halogen-substituted $C_3$–$C_8$ cycloalkyl, or unsubstituted or halogen-substituted phenyl; I-RR represents represents a chiral salen catalyst of formula (1), wherein $R_1$ is a hydrogen atom; I-SS represents a chiral salen catalyst of formula (1), wherein $R_2$ is a hydrogen atom.

The stereoselective hydrolysis of Scheme 2 is described in more detail hereinafter.

Racemic epoxide compound of formula (3), 0.4–0.8 equivalents of water and over 0.001 mol % of a chiral salen catalyst, preferably 0.1–5 mol %, are reacted at a temperature of −10 to 30° C., preferably 5 to 25° C. After the reaction is completed, a chiral epoxide, which is (R)-4 or (S)-4, is obtained by fractional distillation. The chiral salen catalyst is recovered and a chiral 1,2-diol, which is (R)-5 or (S)-5, is obtained from the residue by using organic solvent. The recovered catalyst is re-used for hydrolysis of fresh racemic epoxide to produce chiral epoxide or chiral 1,2-diol without any activation process.

When the chiral salen catalyst of formula (1), where $R_1$ is a hydrogen atom, (hereafter referring to as "I-RR") is used for the stereoselective hydrolysis, (R)-epoxide or (S)-1,2-diol is produced, while when the chiral salen catalyst of formula (1), where $R_2$ is a hydrogen atom, (hereafter referring to as "I-SS") is used, (S)-epoxide or (R)-1,2-diol is produced.

Figure 2:
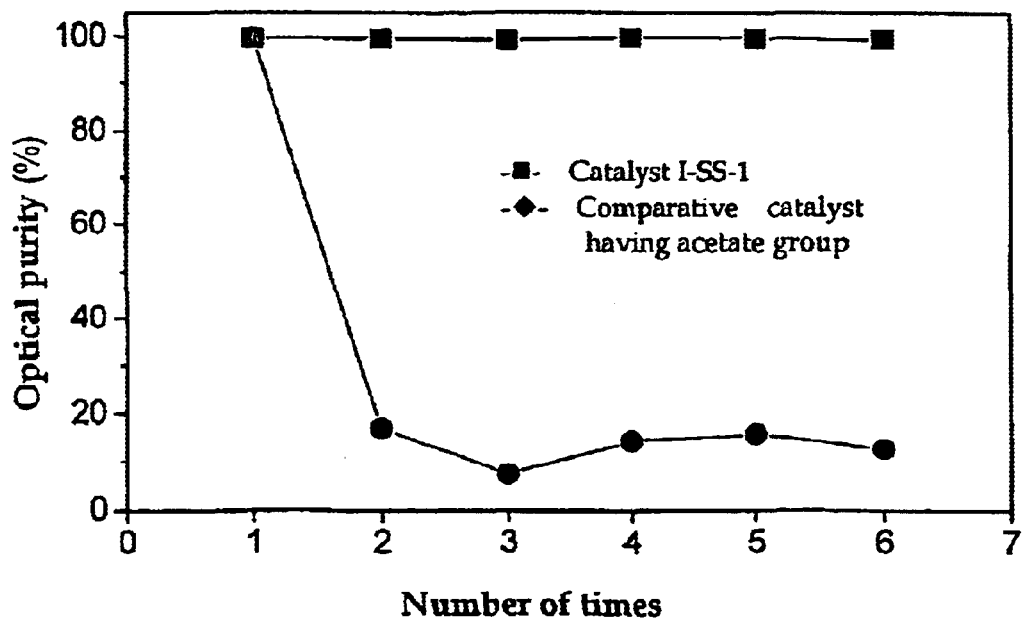
FIG. 2 represents a graph comparing an optical purity of products produced by using conventional chiral salen catalyst having acetate group with that using the chiral salen catalyst of the present invention over number of times it is used.

FIGS. 1 and 2 are graphs comparing a reaction rate and optical purity of conventional chiral salen catalyst having acetate group (comparative catalyst 1) with those of chiral salen catalyst (I-SS-1) of the present invention over reaction time.

Catalyst I-SS-1

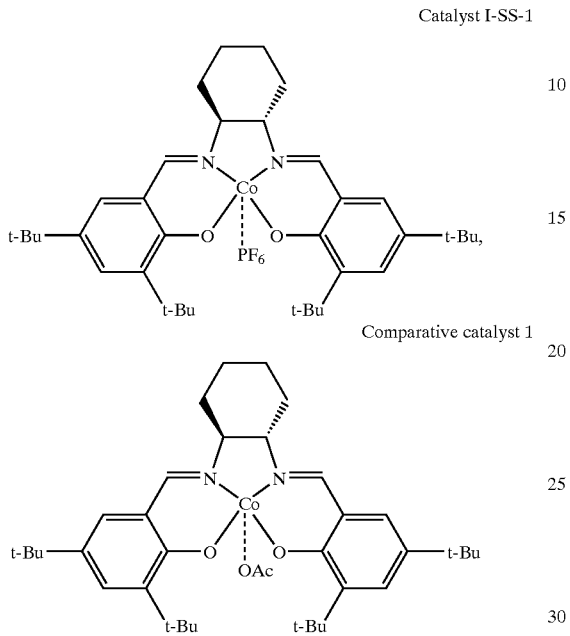

Comparative catalyst 1

The use of the chiral salen catalyst of the present invention shows faster reaction rate and higher optical purity (over 99% ee) than that of the conventional chiral salen catalyst having acetate group. It is further proved that the chiral salen catalyst of the present invention can be used continuously without any activation process, while the conventional chiral salen catalyst having acetate group has to be activated with acetic acid after each use because it looses its catalytic activity and the reaction using recovered catalyst takes much longer to obtain over 99% ee of optical purity of the product than that using fresh catalyst.

Figure 3:
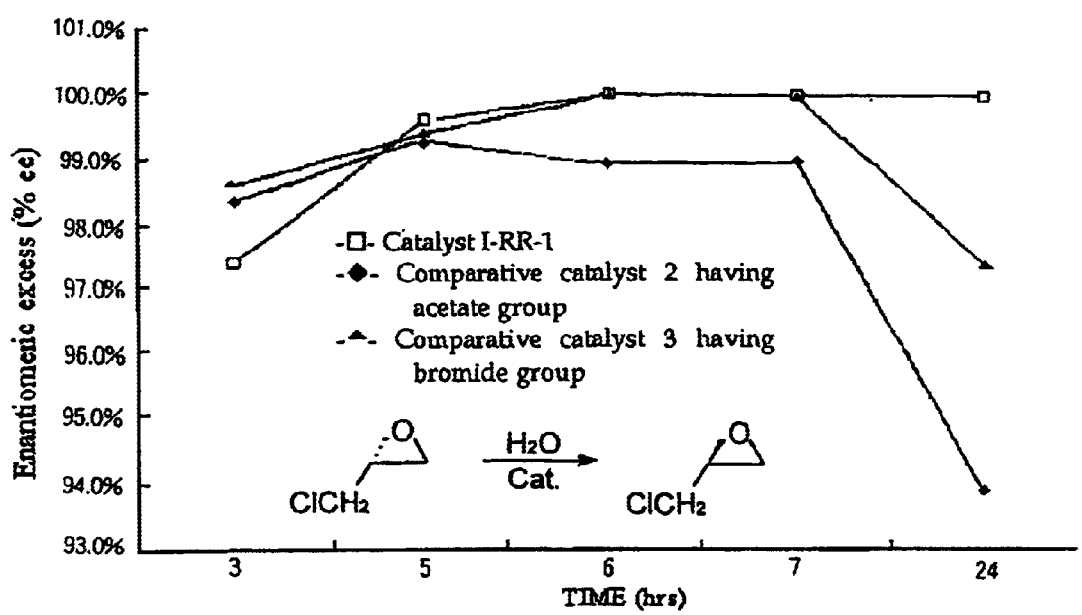
FIG. 3 represents a grape comparing degrees of racemization of products produced by using conventional chiral salen catalyst having acetate group and conventional chiral salen catalyst having bromide group with that using the chiral salen catalyst of the present invention over reaction time.

FIG. 3 represents a graph comparing degrees of racemization of products produced by using conventional chiral salen catalyst having acetate group (OAc; (comparative catalyst 2) and conventional chiral salen catalyst having bromide group (Br; (comparative catalyst 3) with that using the chiral salen catalyst (I-RR-1) of the present invention over reaction time.

Catalyst I-RR-1

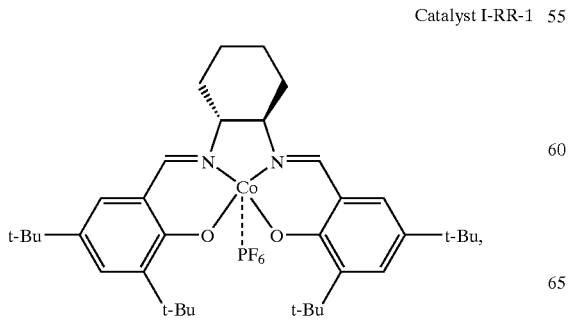

Comparative catalyst 2

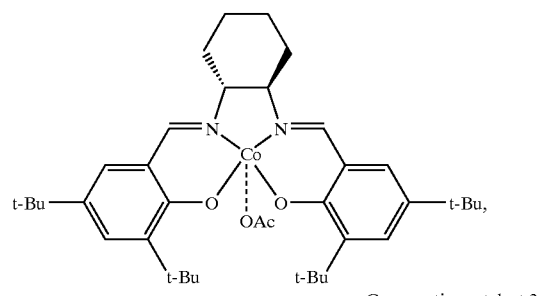

Comparative catalyst 3

In FIG. 3, when the chiral salen catalyst of the present invention is used, there is no or little of racemization over reaction of time, while when conventional chiral salen catalyst having acetate group (OAc; (comparative catalyst 2) or conventional chiral salen catalyst having bromide group (Br; (comparative catalyst 3) is used, the degree of racemization becomes higher over reaction time, resulting in lowering optical purity of the corresponding product because the conventional chiral salen catalysts contain counterions having a nuclophilic group. In the mass production of chiral epoxides, it will take longer reaction time to distill the desired product. Therefore, it is expected that use of the chiral salen catalyst of the present invention contributes to produce optically pure chiral epoxide, while use of the comparative catalyst 2 or 3 produces in lowered optical purity due to racemization during distillation process.

Hereunder is given the more detailed description of the present invention using examples. However, it should not be construed as limiting the scope of the present invention.

EXAMPLE 1

Preparation of (S,S)-N,N'-bis(3,5-di-t-butylsalicylidene)-1,2-cyclohexanediamin cobalt(III) hexafluorophosphate (I-SS-1)

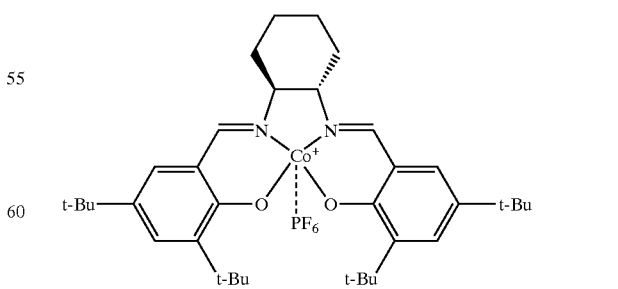

1 Equivalent of (S,S)-N,N'-bis(3,5-di-t-butylsalicylidene)-1,2-cyclohexanediamine and 1,2 equivalent of cobalt(II)acetate.4H$_2$O were added to ethanol and refluxed for 5 hrs while stirring. The reaction mixture was filtered and washed with small amount of ethanol. The obtained solid, 1 equivalent of ferrocenium hexafluorophosphate and acetonitrile were mixed and refluxed for 1 hr while stirring, and acetonitrile was then evaporated under vacuum. Hexane was added to the residue and stirred for 30 min and filtered to obtain the target product. IR 1060, 1110, 1170, 1195, 1210, 1295, 1410, 1480, 1500, 1510, 1605, 1645 cm$^{-1}$; $^{31}$P NMR(CDCl$_3$) δ(H$_3$PO$_4$, ppm)–144.49[m, J($^{31}$P, $^{19}$F)=1.77 KHz]

EXAMPLE 2

Preparation of (R,R)-N,N'-bis(3,5-di-t-butylsalicylidene)-1,2-cyclohexanediamino cobalt(III) hexafluorophosphate (I-RR-1)

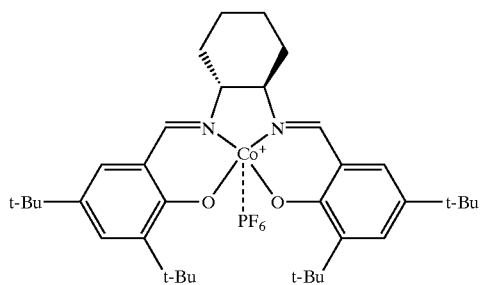

The reaction was performed in the same manner as Example 1 except that (R,R)-N,N'-bis(3,5-di-t-butylsalicylidene)-1,2-cyclohexanediamine was used instead of (S,S)-N,N'-bis(3,5-di-t-butylsalicylidene)-1,2-cyclohexanediamine to obtain the target product. IR 1060, 1110, 1170, 1195, 1210, 1295, 1410, 1480, 1500, 1510, 1605, 1645 cm$^{-1}$; $^{31}$P NMR(CDCl$_3$) δ(H$_3$PO$_4$, ppm)–144.49 [m, J($^{31}$P, $^{19}$F)=1.77 KHz]

EXAMPLE 3

Preparation of (S,S)-N,N'-bis(3,5-di-t-butylsalicylidene)-1,2-cyclohexanediamino cobalt(III) tetrafluoroborate (I-SS-2)

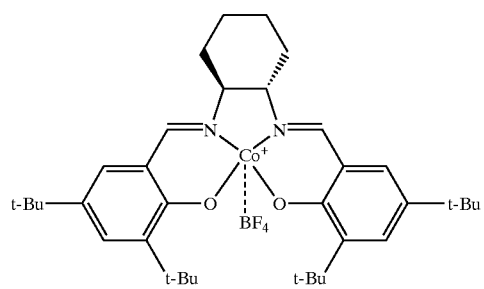

1 Equivalent of (S,S)-N,N'-bis(3,5-di-t-butylsalicylidene)-1,2-cyclohexanediamine and 1.2 equivalents of cobalt(II)acetate.4H$_2$O were added to ethanol and refluxed for 5 hrs while stirring. The reaction mixture was filtered and washed with small amount of ethanol at room temperature. The obtained solid, ferrocenium tetrafluoroborate and acetonitrile were mixed and refluxed for 1 while stirring. Acetonitrile was then evaporated under vacuum. Hexane was added to the residue and stirred for 30 min, followed by filtration to obtain the target product.

EXAMPLE 4

Preparation of (R,R)-N,N'- bis(3,5-di-t-butylsalicylidene)-1,2-cyclohexanediamino cobalt (III) tetrafluoroborate (I-RR-2)

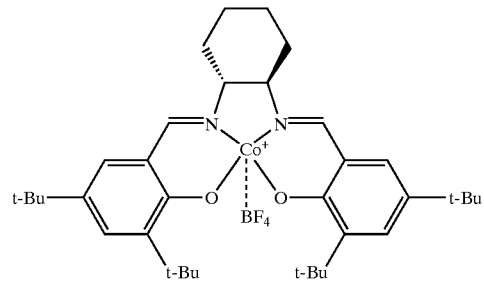

The reaction was performed in the same manner as Example 3 except that (R,R)-N,N'-bis(3,5-di-t-butylsalicylidene)-1,2-cyclohexanediamine was used instead of (S,S)-N,N'-bis(3,5-di-t-butylsalicylidene)-1,2-cyclohexanediamine to obtain the target product.

EXAMPLE 5

Preparation of (S)-N-(3,5-di-t-butylsalicylidene)-(S)-N'-(salicylidene)-1,2-cyclohexanediamino cobalt(III) hexafluorophosphate (I-SS-3)

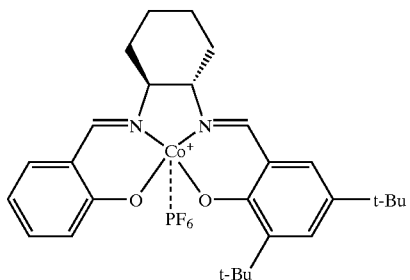

The reaction was performed in the same manner as Example 1 except that (S)-N-(3,5-di-t-butylsalicylidene)-(S)-N'-(salicylidene)-1,2-cyclohexanediamine was used instead of (S,S)-N,N'-bis(3,5-di-t-butylsalicylidene)-1,2-cyclohexanediamine to obtain the target product.
IR 840, 890, 990, 1020, 1110, 1185, 1220, 1255, 1270, 1285, 1370, 1400, 1450, 1480, 1560, 1610, 1640 cm$^{-1}$

EXAMPLE 6

(R)-N-(3,5-di-t-butylsalicylidene)-(R)-N'-(salicylidene)-1,2-cyclohexanediamino cobalt(III) hexafluorophosphate (I-RR-3)

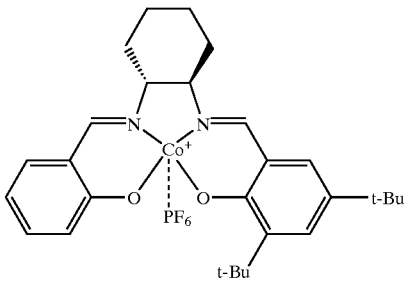

The reaction was performed in the same manner as Example 1 except that (R)-N-(3,5-di-t-butylsalicylidene)-(R)-N'-(salicylidene)-1,2-cyclohexanediamine was used instead of (S,S)-N,N'-bis(3,5-di-t-butylsalicylidene)-1,2-cyclohexanediamine to obtain the target product.

EXAMPLE 7

Preparation of (S)-N-(3,5-di-t-butylsalicylidene)-(S)-N'-(salicylidene)-1,2-cyclohexanediamino cobalt(III) tetrafluoroborate

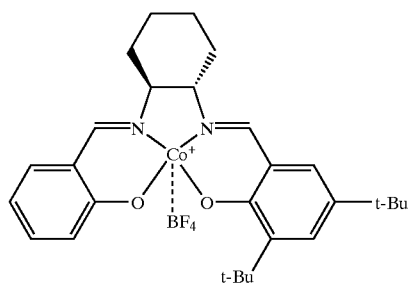

(I-SS-4)

The reaction was performed in the same manner as Example 3 except that (S)-N-(3,5-di-t-butylsalicylidene)-(S)-N'-(salicylidene)-1,2-cyclohexanediamine was used instead of (S,S)-N,N'-bis(3,5-di-t-butylsalicylidene)-1,2-cyclohexanediamine to obtain the target product.

EXAMPLE 8

Preparation of (R)-N-(3,5-di-t-butylsalicylidene)-(R)-N'-(salicylidene)-1,2-cyclohexanediamino cobalt(III) tetrafluoroborte

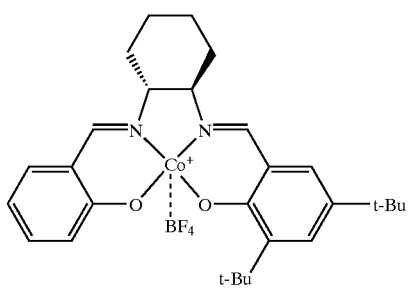

(I-RR-4)

The reaction was performed in the same manner as Example 3 except that (R)-N-(3,5-di-t-butylsalicylidene)-(R)-N'-(salicylidene)-1,2-cyclohexanediamine was used instead of (S,S)-NN'-bis(3,5-di-t-butylsalicylidene)-1,2-cyclohexanediamine to obtain the target product.

EXAMPLE 9

Preparation of (R,R)-N,N'-bis(3,5-di-t-butylsalicylidene)-1,2-cyclohexanediamino cobalt(III) bromide

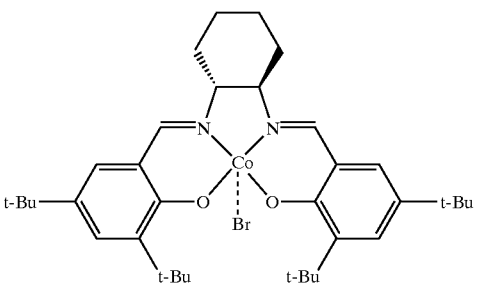

1 equivalent of (R,R)-N,N'-bis(3,5-di-t-butylsalicylidene)-1,2-cyclohexanediamine and 1.2 equivalents of cobalt(II)acetate.4H$_2$O were added to ethanol and refluxed for 5 hrs while stirring. The reaction mixture was filtered and washed with small amount of ethanol at room temperature. The obtained solid, 0.5 equivalents of bromine, and dichloromethane were added and refluxed for 1 hr while stirring and dichloromethane was evaporated under vacuum to obtain the target product.

EXAMPLE 10

Preparation of (R,R)-N,N'-bis(3,5-di-t-butylsalicylidene)-1,2-cyclohexanediamino cobalt (III) chloride

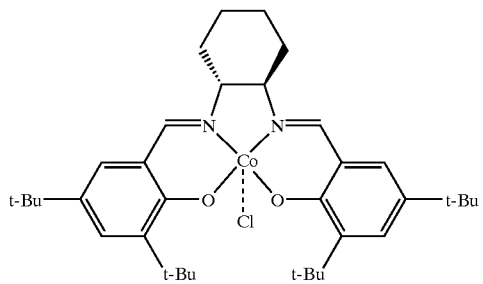

1 equivalent of (R,R)-N,N'-bis(3,5-di-t-butylsalicylidene)-1,2-cyclohexanediamine and 1.2 equivalents of cobalt(II)acetate.4H$_2$O were added to ethanol and refluxed for 5 hrs while stirring. The reaction mixture was filtered and washed with small amount of ethanol at room temperature. The obtained solid, 0.5 equivalents of chlorine gas, and dichloromethane were added and refluxed for 1 hr while stirring and dichloromethane was evaporated under vacuum to obtain the target product.

EXAMPLE 11

Preparation of (R,R)-N,N'-bis(3,5-di-t-butylsalicylidene)-1,2-cyclohexanediamino cobalt(III) iodide

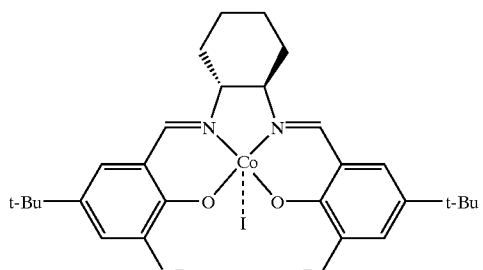

1 equivalent of (R,R)-N,N'-bis(3,5-di-t-butylsalicylidene)-1,2-cyclohexanediamine and 1.2 equivalents of cobalt(II)acetate.4H$_2$O were added to ethanol and refluxed for 5 hrs while stirring. The reaction mixture was filtered and washed with small amount of ethanol at room temperature. The obtained solid, 0.5 equivalents of iodine, and dichloromethane were added and refluxed for 1 hr while stirring and dichloromethane was evaporated under vacuum to obtain the target product.

EXPERIMENTAL EXAMPLE 1

Preparation of (R)-epichlorohydrin or (S)-epichlorohydrin

Each 100 g of racemic epichlorohydrin was added to 0.25 mol % of the catalyst prepared in Examples 1 to 8 and cooled to 5° C. Each 13.6 g of water was added slowly to each reaction mixture and then stirred at 20° C. for 4 hrs. Each reaction mixture was performed for fractional distillation under vacuum to obtain (R)[or (S)]-epichlorohydrin. Dichloromethane and water were added to the residue and the used catalyst was obtained from dichloromethane layer which was further evaporated under vacuum. The recovered catalyst without any activation process was reused for another hydrolysis reaction of racemic epichlorohydrin continuously to obtain (R)[or (S)]-epichlorohydrin with over 99% ee of optical purity.

Figure 4:
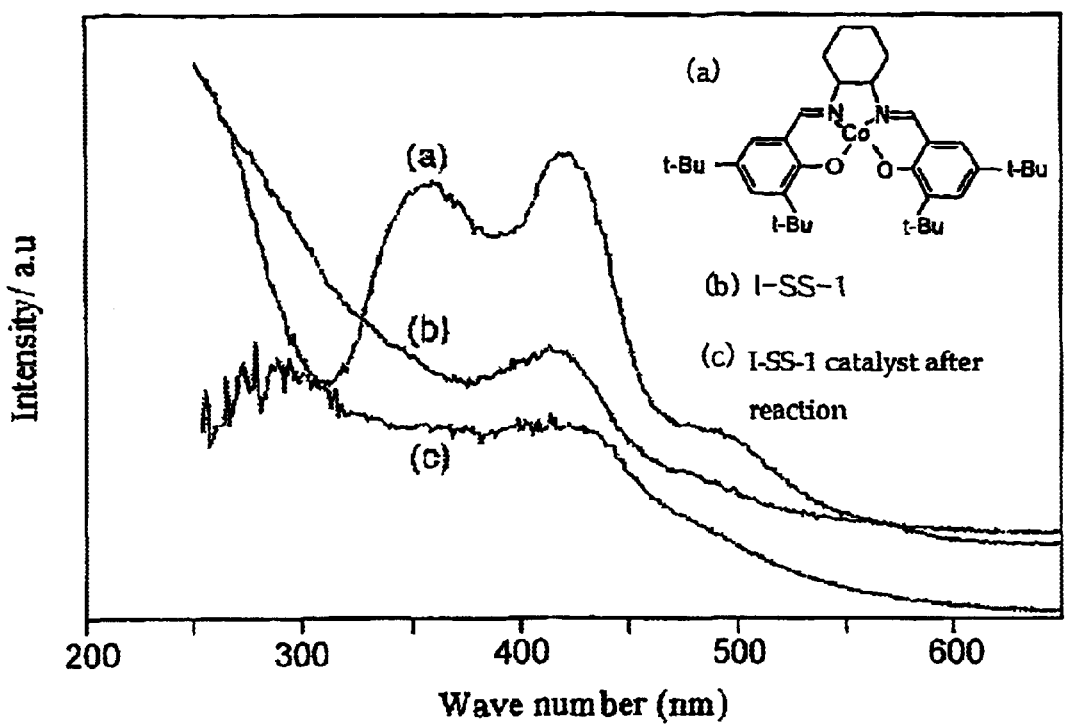
FIG. 4 represents UV data of the catalyst before and after reaction using the chiral salen catalyst of the present invention.

As shown in FIG. 4 representing UV data of I-SS-1 prepared in Example 1 before and after the hydrolysis reaction, the data before the reaction was not changed from that after.

COMPARATIVE EXPERIMENTAL EXAMPLE 1

Preparation of (R)-epichlorohydrin (R)-epichlorohydrin was prepared in the same manner as Experimental Example 1 by using the conventional chiral salen catalyst having acetate group (comparative catalyst 1). When the used catalyst was used for next reaction without any activation process, (R)-epichlorohydrin with 17% ee of optical purity was prepared. After the second reaction, the used catalyst was activated by a known method (*Science*, Vol. 277, 936, 1997). The used catalyst was added in toluene and 2 equivalent of acetic acid and stirred for 1 hr under atmosphere condition and the solvent was then evaporated under vacuum to obtain recovered catalyst. When the third reaction was performed by using the recovered catalyst, the reaction took 7 to 8 hrs under the same reaction condition to obtain (R)-epichlorohydrin with lower than 99% ee of optical purity, while it took only 4 hr when the fresh catalyst was used. The result was summarized in Table 1.

TABLE 1

| Catalyst | Nos. of time | Optical purity (% ee) | Ave. yield | Reaction time |
|---|---|---|---|---|
| Comparative catalyst 1 having acetate group | 1st | >99.8 | 80% | 4 hr |
| | 2nd (w/o activation) | 17 | — | 8 hr |
| | 3rd (w/activation) | <99 | 80% | 8 hr |
| I-SS-1 (or I-RR-1) | 1st | >99.8 | 80.4% | 4 hr |
| | 4th | >99.8 | | 6 hr |
| | 8th | >99.8 | | 8 hr |
| | 10th | >99.4 | | 12 hr |
| I-SS-2 (or I-RR-2) | 1st | >99.8 | 80% | 4 hr |
| | 5th | >99.8 | | 6 hr |
| | 6th | >99.7 | | 10 hr |
| | 7th | >99.4 | | 12 hr |
| I-SS-3 (or I-RR-3) | 1st | >99.8 | 80% | 4 hr |
| | 4th | >99.8 | | 6 hr |
| | 8th | >99.6 | | 8 hr |
| | 10th | >99.3 | | 12 hr |
| I-SS-4 (or I-RR-4) | 1st | >99.8 | 78% | 4 hr |
| | 4th | >99.8 | | 6 hr |
| | 5th | >99.5 | | 8 hr |
| | 6th | >99.1 | | 12 hr |

Figure 5:
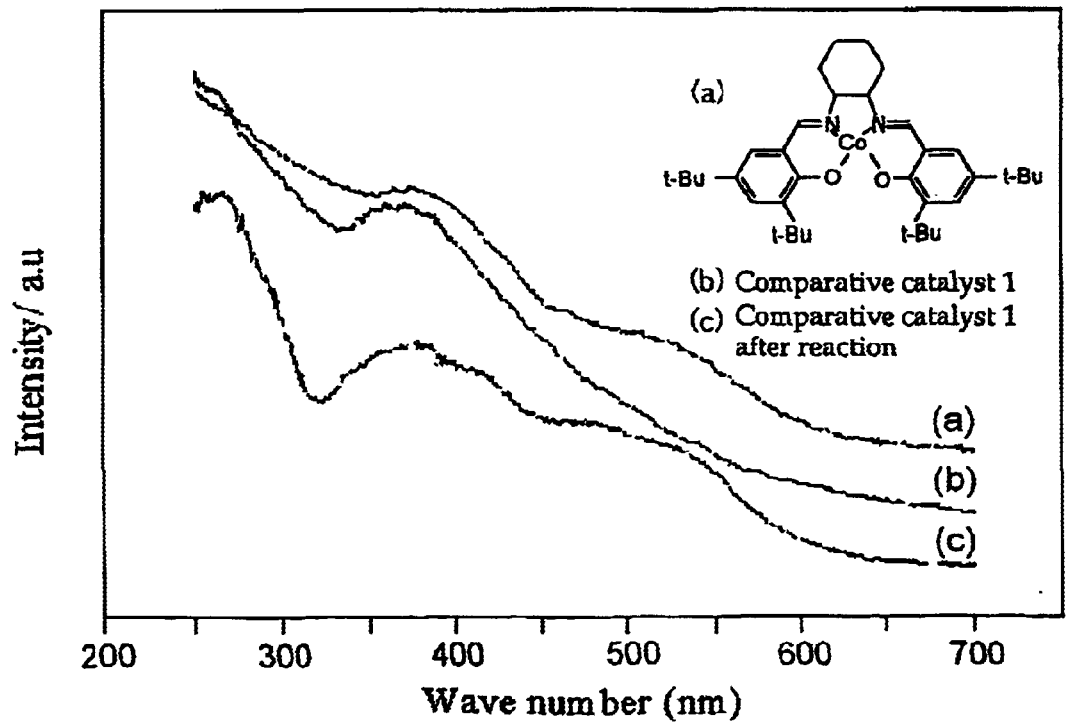
FIG. 5 represents UV data of the catalyst before and after reaction using the chiral salen catalyst having acetate group.

In FIG. 5 representing UV data of the catalyst before and after reaction using the chiral salen catalyst (comparative catalyst 1) having acetate group, it indicated that acetate group of the comparative catalyst 1 was dissociated after the reaction.

COMPARATIVE EXPERIMENTAL EXAMPLE 2

Comparative of Changes in Optical Purity of (S)-epichlorohydrin

Each 0.4 mol % of the catalyst I-SS-1 prepared in Example 2, comparative catalyst 2 having acetate group, and comparative catalyst 3 having bromo group was added to 100 g of racemic epichlorohydrin separately and cooled to 5° C. 10.7 g of water was slowly added to each reaction mixture of which was stirred at 20° C. The optical purity of each reaction mixture was measured over reaction time as shown in FIG. 3.

EXPERIMENTAL EXAMPLE 3

Preparation of (R)-epibromohydrin or (S)-epibromohydrin 2 g of the catalyst prepared in Example 1 (I-SS-1) or Example 2 (I-RR-1) was added to 148 g of racemic epibromohydrin and cooled to 5° C. 13.6 g of water was slowly added to the reaction mixture of which was stirred at 20° C. for 4 hrs. The reaction mixture was performed for fractional distillation under vacuum to obtain (R) (or (S))-epibromohydrin. Dichloromethane and water were added to the residue and extracted out the used catalyst to the dichloromethane layer which was evaporated under vacuum to recover the used catalyst. The recovered catalyst was used for next reaction without any activation process to produce (R) (or (S))-epibromohydrin with over 99% ee of optical purity.

EXPERIMENTAL EXAMPLE 4

Preparation of (S)-1,2-epoxybutane or (R)-1,2-epoxybutane

The reaction was performed in the same manner as Experimental Example 3 except that 78 g of racemic 1,2-epoxybutane was used instead of racemic epibromohydrin to obtain the target product with over 99% ee of optical purity.

EXPERIMENTAL EXAMPLE 5

Preparation of (S)-1,2-epoxyhexane or (R)-1,2-epoxyhexane

The reaction was performed in the same manner as Experimental Example 3 except that 108 g of racemic 1,2-epoxyhexane was used instead of racemic epibromohydrin to obtain the target product with over 99% ee of optical purity.

EXPERIMENTAL EXAMPLE 6

Preparation of (S)-styrene oxide or (R)-styrene oxide 5 g of the catalyst prepared in Example 1 (I-SS-1) or Example 2 (I-RR-1) was added to 130 g of racemic styrene oxide and cooled to 5° C. 13.6 g of water was slowly added to the reaction mixture, which was stirred at 20° C. for 15 hrs. The reaction mixture was performed for fractional distillation under vacuum to obtain first (R) (or (S))-styrene oxide. Dichloromethane and water were added to the residue and extracted out the used catalyst to the dichloromethane layer which was evaporated under vacuum to recover the used catalyst. The recovered catalyst was reused for next reaction without any activation process to produce (R) (or (S))-styrene oxide with over 99% ee of optical purity.

EXPERIMENTAL EXAMPLE 7

Preparation of (S)-1,2-butandiol or (R)-1,2-butandiol 2 g of the catalyst prepared in Example 1 (I-SS-1) or Example 2 (I-RR-1) was added to 78 g of racemic 1,2-epoxybutane and cooled to 5° C. 7.8 g of water was slowly added to the reaction mixture, which was stirred at 20° C. for 3 hrs. The reaction mixture was performed for fractional distillation under vacuum to obtain first (R) (or (S))-1,2-butandiol. Dichloromethane and water were added to the residue and extracted out the used catalyst to the dichloromethane layer which was evaporated under vacuum to recover the used catalyst. The recovered catalyst was reused for next reaction without any activation process to produce (R) (or (S))-1,2-butandiol with over 99% ee of optical purity.

As described above, the chiral salen catalyst of the present invention can be reused without any activation process, which is a disadvantage associated with conventional chiral salen catalyst, and used in mass production of chiral epoxides or chiral 1,2-dials from racemic epoxides in high yield and high optical purity by stereoselective hydrolysis.

What is claimed is:

1. A method of preparing chiral epoxides or chiral 1,2-diols which comprises: stereoselectively hydrolyzing racemic epoxides using a chiral catalyst of formula (1),

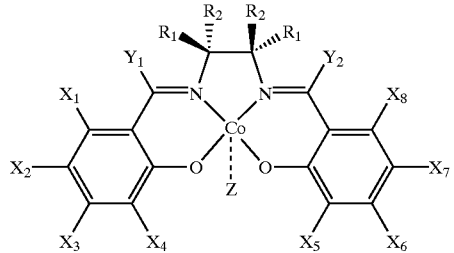

(1)

wherein $X_1$, $X_2$, $X_3$, $X_4$, $X_5$, $X_6$, $X_7$, and $X_8$ represent independently hydrogen or $C_4$–$C_{10}$ alkyl;

$Y_1$ and $Y_2$ represent independently hydrogen or $C_1$–$C_5$ alkyl;

Z represents $PF_6$, or $BF_4$; and $R_1$ and $R_2$ independently represent hydrogen, $C_4$–$C_{10}$ alkyl, unsubstituted phenyl or $C_1$–$C_4$ alkyl substituted phenyl, where one of $R_1$ and $R_2$ should be a hydrogen atom, or $R_1$ and $R_2$ are bonded to be —$(CH_2)_n$— (where n is an integer of 3 to 6) or —$(CH_2)_m$—Q—$(CH_2)_m$— (where m is an integer of 1 to 2 and Q is an oxygen atom or NH).

2. The method of claim 1, wherein said $X_1$, $X_2$, $X_3$, $X_4$, $X_5$, $X_6$, $X_7$, and $X_8$ independently represent a hydrogen atom or t-butyl group;

said $Y_1$ and $Y_2$ represent a hydrogen atom;

said Z represents $PF_6$, or $BF_4$; and one of said $R_1$ and $R_2$ is a hydrogen atom and the other is —$(CH_2)_4$—.

* * * * *